(12) United States Patent
Billis

(10) Patent No.: US 9,180,112 B2
(45) Date of Patent: Nov. 10, 2015

(54) DERMAL COMPOSITIONS CONTAINING GORGONIAN EXTRACT

(75) Inventor: Chris Billis, Buford, GA (US)

(73) Assignee: ERMIS LABS, LLC, Columbia, MD (US)

( * ) Notice: Subject to any disclaimer, the term of this patent is extended or adjusted under 35 U.S.C. 154(b) by 722 days.

(21) Appl. No.: 13/044,311

(22) Filed: Mar. 9, 2011

(65) Prior Publication Data

US 2011/0236499 A1    Sep. 29, 2011

Related U.S. Application Data

(60) Provisional application No. 61/316,827, filed on Mar. 23, 2010.

(51) Int. Cl.
| | | |
|---|---|---|
| *A61K 8/96* | (2006.01) | |
| *A61K 31/327* | (2006.01) | |
| *A61K 35/614* | (2015.01) | |
| *A61Q 19/00* | (2006.01) | |

(52) U.S. Cl.
CPC ............... *A61K 31/327* (2013.01); *A61K 8/965* (2013.01); *A61K 35/614* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 4,745,104 A | 5/1988 | Jacobs et al. | |
| 4,849,410 A | 7/1989 | Jacobs et al. | |
| 5,106,609 A | 4/1992 | Bolich, Jr. et al. | |
| 5,204,093 A | 4/1993 | Victor | |
| 5,420,118 A | 5/1995 | Alban et al. | |
| 5,449,519 A | 9/1995 | Wolf et al. | |
| 5,470,884 A | 11/1995 | Corless et al. | |
| 5,597,808 A | 1/1997 | Haimes et al. | |
| 5,624,911 A | 4/1997 | Fenical et al. | |
| 5,753,245 A | 5/1998 | Fowler et al. | |
| 5,811,114 A | 9/1998 | Knight et al. | |
| 5,827,920 A | 10/1998 | Watanabe et al. | |
| 5,905,091 A | 5/1999 | Fuller | |
| 5,968,528 A | 10/1999 | Deckner et al. | |
| 5,972,359 A | 10/1999 | Sine et al. | |
| 5,997,890 A | 12/1999 | Sine et al. | |
| 6,001,377 A | 12/1999 | SaNogueira, Jr. et al. | |
| 6,022,862 A | 2/2000 | Haimes et al. | |
| 6,046,041 A | 4/2000 | Kerr | |
| 6,120,758 A | 9/2000 | Siddiqui et al. | |
| 6,153,208 A | 11/2000 | McAtee et al. | |
| 6,162,774 A | 12/2000 | Charlton et al. | |
| 6,174,533 B1 | 1/2001 | SaNogueira, Jr. et al. | |
| 6,190,678 B1 | 2/2001 | Hasenoehrl et al. | |
| 6,217,888 B1 | 4/2001 | Oblong et al. | |
| 6,217,913 B1 | 4/2001 | Mohammadi | |
| 6,228,894 B1 | 5/2001 | Rinaldi et al. | |
| 6,238,678 B1 | 5/2001 | Oblong et al. | |
| 6,294,186 B1 | 9/2001 | Beerse et al. | |
| 6,338,855 B1 | 1/2002 | Albacarys et al. | |
| 6,342,208 B1 | 1/2002 | Hyldgaard et al. | |
| 6,416,768 B1 | 7/2002 | Ravaux et al. | |
| 6,423,329 B1 | 7/2002 | Sine et al. | |
| 6,444,647 B1 | 9/2002 | Robinson et al. | |
| 6,475,500 B2 | 11/2002 | Vatter et al. | |
| 6,492,326 B1 | 12/2002 | Robinson et al. | |
| 6,524,598 B2 | 2/2003 | Sunkel et al. | |
| 6,544,562 B2 | 4/2003 | Singh et al. | |
| 6,555,119 B1 | 4/2003 | Mori et al. | |
| 6,585,961 B1 | 7/2003 | Stockel | |
| 6,649,178 B2 | 11/2003 | Mohammadi et al. | |
| 6,680,062 B2 | 1/2004 | Muizzuddin et al. | |
| 6,699,488 B2 | 3/2004 | Deckner et al. | |
| 6,780,622 B2 | 8/2004 | Kerr et al. | |
| 6,787,571 B2 | 9/2004 | Jacobs et al. | |
| 6,927,205 B2 | 8/2005 | Patt | |
| 6,974,799 B2 | 12/2005 | Lintner | |
| 6,998,113 B1 | 2/2006 | Traynor et al. | |
| 7,025,952 B1 | 4/2006 | Traynor et al. | |
| 7,037,513 B1 | 5/2006 | Traynor et al. | |
| 7,060,686 B2 | 6/2006 | Jacobs et al. | |

(Continued)

FOREIGN PATENT DOCUMENTS

| | | |
|---|---|---|
| EP | 0831851 B1 | 11/2002 |
| EP | 1441685 B1 | 11/2008 |

OTHER PUBLICATIONS

Onumah, N., et al., "A Novel Anti-Inflammatory in Treatment of Acne Vulgaris: The Pseudopterosins", "Journal of Drugs in Dermatology", Oct. 2013, pp. 1177-1179, vol. 12, No. 10.

Correa, H., et al., "Anti-inflammatory effects of the gorgonian Pseudopterogorgia elisabethae collected at the Islands of Providencia and . . . ", "Journal of Inflammation", Mar. 2009, pp. 5-15, vol. 6, No. 1.

(Continued)

*Primary Examiner* — Terry A McKelvey
*Assistant Examiner* — Catheryne Chen
(74) *Attorney, Agent, or Firm* — Hultquist, PLLC; Steven J. Hultquist; Mary B. Grant

(57) ABSTRACT

A skincare composition comprising Gorgonian extract as an anti-inflammatory component thereof, said skincare composition being selected from among compositions (I) and (II): (I) an aqueous composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %; and (II) a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

20 Claims, No Drawings

(56) References Cited

U.S. PATENT DOCUMENTS

| | | | |
|---|---|---|---|
| 7,098,189 B2 | 8/2006 | Malik | |
| 7,108,860 B2 | 9/2006 | Dueva et al. | |
| 7,208,460 B2 | 4/2007 | Shefer et al. | |
| 7,217,690 B2 | 5/2007 | McGrath | |
| 7,226,581 B2 | 6/2007 | Traynor et al. | |
| 7,226,582 B2 | 6/2007 | Traynor et al. | |
| 7,235,249 B2 | 6/2007 | Bissett | |
| 7,285,570 B2 | 10/2007 | Robinson et al. | |
| 7,338,793 B2 | 3/2008 | Kerr et al. | |
| 7,354,926 B2 | 4/2008 | Lintner | |
| 7,396,526 B1 | 7/2008 | Cole et al. | |
| 7,531,185 B2 | 5/2009 | Chen et al. | |
| 7,544,375 B1 | 6/2009 | Bellin et al. | |
| 7,608,642 B2 | 10/2009 | Malik | |
| 2003/0049212 A1* | 3/2003 | Robinson et al. | 424/59 |
| 2003/0068343 A1* | 4/2003 | Muizzuddin et al. | 424/401 |
| 2003/0072777 A1 | 4/2003 | Maes et al. | |
| 2003/0232091 A1 | 12/2003 | Shefer et al. | |
| 2005/0147631 A1 | 7/2005 | Goldstein et al. | |
| 2006/0198800 A1 | 9/2006 | Dilallo et al. | |
| 2007/0048234 A1* | 3/2007 | Waugh et al. | 424/61 |
| 2007/0281026 A1 | 12/2007 | Vyavahare et al. | |
| 2008/0102045 A1 | 5/2008 | Shim | |
| 2009/0035392 A1 | 2/2009 | Wilkinson | |
| 2009/0162304 A1 | 6/2009 | DiLeva | |
| 2009/0214607 A1 | 8/2009 | Lintner et al. | |
| 2009/0214654 A1 | 8/2009 | Isenburg et al. | |

OTHER PUBLICATIONS

Kijjoa, A., et al., "Drugs and Cosmetics from the Sea", "Marine Drugs", May 2004, pp. 73-82, vol. 2.

Kim, K., "Antimicrobial Activity in Gorgonian Corals (Coelenterata, Octocorallia)", "Coral Reefs", May 1994, p. 75 vol. 13, No. 2.

* cited by examiner

DERMAL COMPOSITIONS CONTAINING GORGONIAN EXTRACT

CROSS REFERENCE TO RELATED APPLICATIONS

The benefit of priority under 35 USC 119 of U.S. Provisional Patent Application 61/316,827 filed Mar. 23, 2010 in the name of Chris Billis for "DERMAL COMPOSITIONS CONTAINING GORGONIAN EXTRACT" is hereby claimed. The disclosure of such provisional U.S. Patent Application is hereby incorporated herein by reference, for all purposes.

FIELD

The present invention relates to dermal compositions for topical administration to enhance skin condition and combat skin disorders such as acne, dermatitis, rosacea and the like.

DESCRIPTION OF THE RELATED ART

In the use of field of skin care, a wide variety of products have been developed and commercialized for enhancing skin condition, e.g., for combating adverse dermal disorders such as dermatitis, acne, rosacea, and the like. Such products have taken various forms, including, without limitation, facial and skin powders, gels, plasters, saturated wraps, cremes, rinses, film-forming compositions, transdermal patches, aerosolized sprays, mud formulations, salves, slurries, and pastes.

These skin products have used a variety of active ingredients, including retinol and retinoids generally, benzoyl peroxide, hexachlorophene, and numerous others.

The art is continually seeking new dermal formulations that are storage stable, easily applied to the skin, and effective to combat a variety of skin disorders including acne, rosacia and dermatitis.

SUMMARY

The present invention relates to skin care compositions for topical administration, which are therapeutically effective for conditioning the skin and combating skin disorders including those discussed in the Background section hereof.

In one aspect, the invention relates to a skincare composition comprising Gorgonian extract as an anti-inflammatory component thereof, such skincare composition being selected from among compositions (I) and (II):

(I) an aqueous composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %; and (II) a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

In another aspect, the invention relates to an aqueous composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %.

In a further aspect, the invention relates to a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

In a still further aspect, the invention relates to a method of enhancing skin condition, comprising topically administering to skin in need thereof, a skincare composition comprising Gorgonian extract as an anti-inflammatory component thereof, said skincare composition being selected from among compositions (I) and (II):

(I) an aqueous composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %; and (II) a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

Other aspects, features and embodiments of the invention will be more fully apparent from the ensuing disclosure and appended claims.

DETAILED DESCRIPTION

The present invention relates to skin treatment compositions that are topically administered to improve the character of the skin, and to combat adverse skin conditions such as acne, dermatitis, and inflammatory dermatoses.

As used herein, references to compositional ingredients in percents by weight refers to weight percentages based on the total weight of the composition or formulation.

Dermatological compositions of the invention may be utilized for treatment of a wide variety of dermal conditions and adverse physiological states manifesting dermally, including, without limitation, dry skin/xerosis, psoriasis, ichthoyosis, keratosis, keratoderma, dermatitis, pruritis, eczema, and acne. Compositions of the invention are usefully employed as skin moisturizers, skin softening agents, skin debridement agents, etc. In cosmetic formulations, the compositions of the invention may be used with added ingredients that are solely cosmetic. Alternatively, the cosmetic formulation may include ingredients that are both cosmetically efficacious and therapeutically effective, e.g., so-called "cosmeceutical" ingredients.

In various embodiments of the invention, the compositions described herein may comprise, consist or consist essentially of the specified ingredients or specific ones thereof. Further, it will be understood that the formulations of the invention may be widely varied, as regards the absolute amounts and relative proportions thereof, in relation to specific examples, and illustrative compositions.

The present invention contemplates two principal types of skin care compositions utilizing Gorgonian extract as an anti-inflammatory component thereof.

The first type of composition is a face wash composition, which as a result of the presence of Gorgonian extract is able to utilize retinol in a highly effective manner in compositions containing very high concentrations of water and surfactant components, e.g., compositions in which water and surfactant components together constitute from 60 to 95 percent by weight (wt. %) of the total composition, more preferably from 65 wt. % to 90 wt. %, and most preferably from 75 to 88 wt. %, on the same total weight of the composition basis, and wherein the weight of surfactant to weight of water is in a ratio of from 0.40 to 1.3, more preferably from 0.5 to 1.0, and most preferably from 0.6 to 0.8. In various embodiments of the invention, the amount of water in the composition is from 35 wt. % to 65 wt. %, more preferably from 40 to 60 wt. %, and most preferably from 45 to 55 wt. %, based on the total weight of the composition.

The face wash formulations of the invention in specific embodiments thereof may contain retinol in the range of from 0.01 to 0.2 wt. %, based on the total weight of the composition, more preferably from 0.02 to 0.1 wt. %, and most preferably from 0.25 to 0.06 wt. %, on the same total composition weight basis. The Gorgonian extract may be present in the face wash composition in amounts of from 0.005 to 0.5 wt. %, more preferably from 0.01 to 0.1 wt. %, and most preferably from 0.02 to 0.05 wt. %, on the same total composition weight basis.

The amount of Gorgonian extract in the wash composition may broadly be from 2 to 10 times the amount of retinol in the composition, more preferably from 2.5 to 5 times the amount of retinol in the composition, and most preferably from 3 to 4 times the amount of retinol in the composition, on a weight or a weight percent basis, wherein weights are in the same units, and weight percent is based on total weight of the composition, for each of the two ingredients.

The retinol wash compositions of the invention in specific embodiments may contain water and surfactant ingredients that together constitute from 60 to 95 wt. % of the wash composition, based on total weight thereof. More preferably, the water and surfactant ingredients in such embodiments constitute from 65 to 90 wt. % of the wash composition, and most preferably from 75 to 85 wt. %, on the same composition total weight basis.

Outside of the broadest of the foregoing compositional ranges, the composition tends to become markedly less effective as a face wash composition, with respect to cleansing abilities of the composition, or with respect to undesirably high stringency of the retinol active ingredient or retinoic acid byproducts thereof on the skin surface subsequent to administration.

In this respect, the present invention achieves a therapeutically effective delivery of retinol that avoids skin sensitivity complications of itching, stinging, rashes, etc. that sometimes accompany relatively high dosages of retinol in skin care compositions of the prior art.

The water used as the principal ingredient in the retinol wash composition is preferably of a highly purified form, and may for example be singly or multiply distilled water that is submitted to additional purification treatment such as filtration, ion exchange treatment, etc.

The surfactant ingredient utilized in the retinol wash composition may include single or multicomponent surfactant species. In various compositional embodiments, the amount of the surfactant may range from 25 to 45 wt. %, based on total weight of the composition, more preferably from 30 to 40 wt. %, and most preferably from 32 to 38 wt. %, based on total weight of the composition. Any suitable surfactants species may be employed that are compatible with the other ingredients of the formulation and provide suitable use and therapeutic benefit characteristics. Illustrative surfactants that may be employed in the broad practice of the invention include, without limitation, sodium laureth sulfate, cocamidopropyl betaine, disodium laureth sulfosuccinate, lauryl betaine, disodium laureth sulfosuccinate, peg-10 soy sterol, sodium cocoate, sodium dodecylbenzene sulfonate, and sodium stearate. Particularly preferred surfactant species include sodium laureth sulfate, commercially available from Cognis/DeWolf under the trademark STANDAPOL ES2, and cocamidopropyl betaine, commercially available from Cognis/DeWolf under the trademark VELVETEX BK 35.

The retinol ingredient may be provided as a pure single component ingredient, or as one component of a multicomponent ingredient, including for example the retinol in a vehicle or carrier composition that may for example include preservatives, polymers and emollients, as well as other ingredients. A preferred retinol multicomponent ingredient is available from Tagra under the trademark TAGRAVIT R1, which contains retinol, polymethylmethacrylate, butyl hydroxy toluene (BHT) and tricaprylin, a mixture of glycerin and caprylic acid.

The Gorgonian extract, sometimes referred to as sea whip extract, contains caprylic and capric triglycerides. A preferred Gorgonian extract is commercially available from Lipo as Gorgonian Extract GC.

In addition to the principal ingredients of water, surfactant, retinol and Gorgonian extract, the retinol wash compositions of the invention may contain any vehicular or carrier components, additives, excipients, and functional components to improve application and/or performance properties of the composition.

The retinol wash composition may for example contain thickener, humectant and emollient components, and the combination of such ingredients in various specific embodiments of the invention may constitute from 5 to 20 wt. % of the total composition weight, more preferably from 7.5 to 17.5 wt. %, and most preferably from 8 to 15 wt. %, on the same total composition weight basis.

Such thickener, humectant and emollient components may be of any suitable type or types, and single component as well as multicomponent ingredients are contemplated within the broad scope of the invention.

Thickener ingredients may for example comprise polysaccharides, carbomers, starches, gums, waxes, sorbitols, cellulosic materials, polymers, clays, silica, or any other useful for getting materials. A preferred thickener in retinol wash compositions of the invention is acrylate copolymer commercially available under the trademark CARBOPOL AQUA SF-1 from Lubrizol/Protameen.

Humectants useful in the retinol wash compositions of the invention may be of any suitable type, and for example may include glycerin, propylene glycol, alpha hydroxy acids, glyceryl triacetate, polyols, sorbitol, xylitol, maltitol, polydextrose, quillaia, lactic acid, urea, and the like. A preferred humectant is glycerin USP grade.

Emollients employed in the retinol wash compositions of the invention can be of widely varying types, including, for example, aloe vera, jojoba oil, soybean oil, silicones, hydrocarbons, alkylene oxide copolymers, lanolin, squalene, tocopherols, phytosterols, and the like. A preferred emollient class is dimethicone emollients, with PEG-8 dimethicone, commercially available under the trademark ZENICONE DMC-1 from Zenitech being a preferred emollient species.

In addition to thickeners, humectants and emollients, retinol wash compositions of the invention may in specific embodiments contain pH adjusting agents, including both acid and base pH adjustment agents, such as citric acid, sodium hydroxide, etc., wherein acid and base species may be in suitable aqueous solution, and additional or alternative ingredients, including, without limitation, preservatives, foaming agents and foaming boosters, fragrances, exfoliants, and colorants.

In specific embodiments, the wash composition may be formulated to have a pH of between 6 and 7, and a viscosity in a range of from 3000 to 4500 centipoise, as measured by a No. 4 Brookfield spindle at a rotational speed of 20 RPM.

Compositions of the invention may be made up in simple mixing/blending operations, using slow speed agitation to avoid excessive aeration, with gentle heating optionally being employed to solubilize and homogenize specific ingredients as necessary.

The wash composition of the invention may be applied by hand, or by an absorptive applicator such as a pad, sponge or the like, to facial or other skin areas. The composition once applied may be retained on the skin and allowed to dry thereon, or it may be blotted or otherwise rinsed away with water after a short residence time on the skin, e.g., a period of from 30 seconds to several minutes.

The wash composition may be packaged in a rigid or squeeze bottle, and the container may be equipped with an aerosol or pump head to facilitate dispensing. Alternatively, the wash composition may be impregnated in a pad or sponge applicator that is packaged for single use application by a user. The package may contain use instructions and normal packaging indicia.

The other principal type of skin care composition of the invention is a gel serum composition containing Gorgonian extract in combination with benzoyl peroxide as active ingredients.

In such a gel serum composition, use of Gorgonian extract permits high levels of benzoyl peroxide to be employed, e.g., from 1 to 12 wt. %, based on total weight of the composition, in gel formulations containing high levels of water to enable highly effective skin hydration to be achieved concurrently with the therapeutic effect of benzoyl peroxide.

The gel serum compositions of the invention in various embodiments may contain from 60 to 90 wt. % water, based on total weight of the composition, more preferably from 65 to 85 wt. % water, and most preferably from 70 to 80 wt. %, on the same total composition weight basis.

Gel serum compositions in various formulations may contain benzoyl peroxide in an amount of from 1 to 12 wt. %, based on total weight of a composition, more preferably from 2 to 10 wt. %, and most preferably from 5 to 8 wt. %, on the same total weight composition basis.

Gel serum formulations in various embodiments may contain from 0.05 to 1.25 wt. % Gorgonian extract, more preferably from 0.1 to 1.0 wt. %, and most preferably from 0.2 to 0.75 wt. %, on the same total weight composition basis.

In various embodiments of the invention, the total amount of benzoyl peroxide and Gorgonian extract is from 2 to 15 wt. %, based on total weight of the composition, more preferably from 4 to 12 wt. %, and most preferably from 5 to 10 wt. %, on the same total composition weight basis.

In various embodiments of the invention, the ratio of benzoyl peroxide to Gorgonian extract may be in a range of from 5 to 20, more preferably from 8 to 18, and most preferably from 10 to 15, when the ratio is calculated as a weight ratio with benzoyl peroxide and Gorgonian extract expressed in the same weight units or weight percentages.

In still other embodiments of the invention, the gel serum composition may contain thickener, humectant and emollient components, in which the total weight percent of such components, based on total weight of the composition, is in the range of from 2 to 18 wt. %, more preferably from 4 to 15 wt. %, and most preferably from 6 to 12 wt. %. It will be recognized that one or multiple species of each of such components may be employed in the composition.

Outside of the broadest of the foregoing compositional ranges, the gel serum composition tends to become markedly less effective, with respect to skin conditioning abilities of the composition, or with respect to the therapeutic effect of the benzoyl peroxide active ingredient.

The aforementioned thickener, humectant and emollient components may be of any suitable type or types, and single component as well as multicomponent ingredients are contemplated within the broad scope of the invention.

Thickener ingredients may for example comprise polysaccharides, carbomers, starches, gums, waxes, sorbitols, cellulosic materials, polymers, clays, silica, or any other useful for getting materials. Preferred thickener ingredients in gel serum compositions of the invention include acrylates/$C_{10\text{-}30}$ alkyl acrylate crosspolymer commercially available under the trademark PEMULEN TR1, carbomer commercially available under the trademark CARBOPOL ULTREZ 10 Polymer, and acrylates/$C_{10\text{-}30}$ alkyl acrylate crosspolymer commercially available under the trademark CARBOPOL ULTREZ 21 Polymer, all from Lubrizol/Protameen.

Humectants useful in the benzoyl peroxide gel serum compositions of the invention may be of any suitable type, and for example may include glycerin, propylene, alpha hydroxy acids, glyceryl triacetate, polyols, sorbitol, xylitol, maltitol, polydextrose, quillaia, lactic acid, urea, and the like. Preferred humectants include glycerin USP grade and pentylene glycol.

Emollients employed in the benzoyl peroxide gel serum compositions of the invention can be of widely varying types, including, for example, aloe vera, jojoba oil, soybean oil, silicones, hydrocarbons, alkylene oxide copolymers, lanolin, squalene, tocopherols, phytosterols, and the like. A preferred emollient class is dimethicone and trimethicone emollients, with dimethicone, a silicone emollient commercially available under the trademark DC 200 Fluid 100 CST from Dow Corning/Univar, and phenyl trimethicone, a silicone emollient commercially available under the trademark DC 556 Fluid from Dow Corning being preferred emollient species.

The Gorgonian extract, or sea whip extract, contains caprylic and capric triglycerides. A preferred Gorgonian extract is commercially available from Lipo as Gorgonian Extract GC.

A preferred benzoyl peroxide ingredient for use in the benzoyl peroxide gel serum compositions of the invention is the benzoyl peroxide commercially available from a Sigma-Aldrich/Arkema as Luperox A75FP, #513474.

In addition to thickeners, humectants and emollients, benzoyl peroxide serum gel compositions of the invention may in specific embodiments contain pH adjusting agents, including both acid and base pH adjustment agents, such as citric acid, sodium hydroxide, etc., wherein acid and base species may be in suitable aqueous solution, and additional or alternative ingredients, including, without limitation, preservatives, penetration enhancers, chelating agents, fragrances, exfoliants, and colorants.

In specific embodiments, the benzoyl peroxide gel serum composition may be formulated to have a pH of between 5 and 6, and a viscosity in a range of from 20,000 to 40,000 centipoise, as measured under temperature-controlled conditions (Brookfield TC unit) at a rotational speed of 5 RPM.

The benzoyl peroxide gel serum compositions of the invention may be made up in simple mixing/blending operations, using slow speed agitation to avoid excessive aeration, with gentle heating optionally being employed to solubilize and homogenize specific ingredients as necessary.

The benzoyl peroxide gel serum compositions of the invention may be applied by hand, or by an applicator such as a pad, sponge or the like, to facial or other skin areas. The composition once applied may be retained on the skin for a predetermined period of time achieving the desired therapeutic benefit, and thereafter it may be wiped or otherwise rinsed away with water or other suitable removal medium.

The gel serum composition may be packaged in a rigid or squeeze bottle, and the container may be equipped with a pump head to facilitate dispensing. Alternatively, the gel serum composition may be impregnated in a pad, cloth or sponge applicator that is packaged for single use application by a user. The package may contain use instructions and normal packaging indicia.

Thus, the invention contemplates skincare compositions comprising Gorgonian extract as an anti-inflammatory component thereof, in which such skincare composition is selected from among compositions (I) and (II):

(I) an aqueous composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %; and (II) a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

The aforementioned aqueous composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %, provides a composition useful for skin wash, e.g., face wash, purposes.

Such skincare composition may comprise an aqueous composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %. The skincare composition may be formulated, wherein the water and surfactant together constitute from 60 to 95 percent by weight (wt. %) of the total composition, more preferably from 65 to 90 percent by weight (wt. %) of the total composition, and most preferably from 75 to 88 percent by weight (wt. %) of the total composition.

The weight of surfactant to weight of water in such skincare composition may be in a ratio of from 0.40 to 1.3, from 0.5 to 1.0, or from 0.6 to 0.8, in various embodiments. The composition may contain water in an amount from 40 to 60 wt. %, based on the total weight of the composition, or from 45 to 55 wt. %, based on the total weight of the composition, in respective embodiments. A retinol may be contained in the composition in a range of from 0.02 to 0.1 wt. %, based on the total weight of the composition, or from 0.25 to 0.06 wt. %, based on the total weight of the composition, in respective embodiments. Gorgonian extract may be present in the composition in an amount of from 0.01 to 0.1 wt. %, based on total weight of the composition, or in an amount of from 0.02 to 0.05 wt. %, based on total weight of the composition, in respective embodiments. The amount of Gorgonian extract in the composition may be from 2 to 10 times the amount of retinol in the composition, from 2.5 to 5 times the amount of retinol in the composition, or from 3 to 4 times the amount of retinol in the composition, in various embodiments.

The skincare composition may be formulated so that the water and surfactant together constitute from 60 to 95% wt. % of the wash composition, based on total weight thereof, or from 65 to 90 wt. % of the wash composition, based on total weight thereof, or from 75 to 85 wt. % of the wash composition, based on total weight thereof, in respective embodiments. The amount of surfactant in the skincare composition may be from 30 to 40 wt. %, based on total weight of the composition, or from 32 to 38 wt. %, based on total weight of the composition, in respective embodiments. Surfactants useful in the skincare composition include sodium laureth sulfate, cocamidopropyl betaine, disodium laureth sulfosuccinate, lauryl betaine, disodium laureth sulfosuccinate, peg-10 soy sterol, sodium cocoate, sodium dodecylbenzene sulfonate, and sodium stearate, with sodium laureth sulfate and cocamidopropyl betaine being usefully employed in combination.

The skincare composition may further include thickener, humectant and emollient ingredients, e.g., wherein such ingredients together constitute from 5 to 20 wt. % of the total composition weight, from 7.5 to 17.5 wt. % of the total composition weight, or from 8 to 15 wt. % of the total composition weight, in various embodiments. Thickeners may be employed in the skincare composition, such as polysaccharides, carbomers, starches, gums, waxes, sorbitols, cellulosic materials, polymers, clays, and silica, with an acrylate copolymer thickener being preferred. The skincare composition may be formulated with a humectant selected from among glycerin, propylene glycol, alpha hydroxy acids, glyceryl triacetate, polyols, sorbitol, xylitol, maltitol, polydextrose, quillaia, lactic acid, and urea, with glycerin being preferred. In emollients, such as aloe vera, jojoba oil, soybean oil, silicones, hydrocarbons, alkylene oxide copolymers, lanolin, squalene, tocopherols, phytosterols, and mixtures thereof may be employed in the composition, e.g., a dimethicone emollient.

The skincare wash composition may include one or more ingredients such as pH adjusting agents, preservatives, foaming agents, foaming boosters, fragrances, exfoliants, and colorants. The composition may have a pH of between 6 and 7, and/or a viscosity in a range of from 3000 to 4500 centipoise, as measured by a No. 4 Brookfield spindle at a rotational speed of 20 RPM.

Gel compositions of the invention are contemplated, comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

In specific embodiments, the gel composition may include from 65 to 85 wt. % water, based on weight of the gel composition, or from 70 to 80% wt. % water, based on weight of the gel composition, in respective embodiments. The gel composition may contain benzoyl peroxide in an amount of from 2 to 10 wt. %, based on weight of the gel composition, or in an amount of from 5 to 8 wt. %, based on weight of the gel composition, in respective embodiments. The amount of Gorgonian extract in the gel composition may be from 0.1 to 1.0 wt. %, based on weight of the gel composition, or from 0.2 to 0.75 wt. %, based on weight of the gel composition, in respective embodiments.

The gel composition may be formulated to contain a total amount of benzoyl peroxide and Gorgonian extract of from 2 to 15 wt. %, based on total weight of the composition, from 4 to 12 wt. %, based on total weight of the composition, or from 5 to 10 wt. %, based on total weight of the composition, in various embodiments. The weight ratio of benzoyl peroxide to Gorgonian extract in the gel compositions of the invention may be in a range of from 5 to 20, or from 8 to 18, or from 10 to 15, in respective embodiments.

Formulations of the gel composition may further include thickener, humectant and emollient components, e.g., compositions in which the thickener, humectant and emollient components have a total weight in a range of from 2 to 18 wt. %, based on total weight of the composition, or from 4 to 15 wt. %, based on total weight of the composition, or from 6 to 12 wt. %, based on total weight of the composition, in various embodiments. The gel composition can include a thickener selected from among polysaccharides, carbomers, starches, gums, waxes, sorbitols, cellulosic materials, polymers, clays, and silica, e.g., a thickener including acrylates/$C_{10-30}$ alkyl acrylate crosspolymer, carbomer, and acrylates/$C_{10-30}$ alkyl acrylate crosspolymer.

A humectant may be included in the gel composition, selected from among glycerin, propylene, alpha hydroxy acids, glyceryl triacetate, polyols, sorbitol, xylitol, maltitol, polydextrose, quillaia, lactic acid, and urea, e.g., a humectant including glycerin and pentylene glycol.

An emollient may be included in the gel composition, selected from among aloe vera, jojoba oil, soybean oil, silicones, hydrocarbons, alkylene oxide copolymers, lanolin, squalene, tocopherols, and phytosterols, such as an emollient including dimethicone and trimethicone emollient species, e.g., an emollient including dimethicone and phenyl trimethicone emollient species. Compositions may further include additional ingredients such as pH adjustment agents, preservatives, penetration enhancers, chelating agents, fragrances, exfoliants, and colorants. The gel composition may have a pH of between 5 and 6, and/or a viscosity in a range of from 20,000 to 40,000 centipoise, as measured under temperature-controlled conditions (Brookfield TC unit) at a rotational speed of 5 RPM.

The advantages and features of the invention are further illustrated with reference to the following examples, which are not to be construed as in any way limiting the scope of the invention but rather as illustrative of embodiments of the invention in specific applications thereof.

Example 1

A face wash formulation was made up with the composition set out in Table 1 below.

TABLE 1

0.03% Retinol Wash Formulation

| Ingredient | Weight % | Function |
|---|---|---|
| Water | 50.2 | solvent/diluent |
| Acrylate Copolymer | 8.0 | thickener |
| Sodium Laureth Sulfate | 30.0 | surfactant |
| 20% NaOH Solution (aq) | 1.3 | pH adjusting agent |
| Cocamidopropyl betaine | 5.0 | surfactant |
| Glycerin | 2.5 | humectant |
| PEG-8 dimethicone | 1.0 | emollient |
| Chlorphenesin | 0.2 | preservative |
| Methylisothiazolinone | 0.1 | preservative |
| Cocamide MEA | 0.5 | foaming agent/foaming booster |
| Fragrance | 0.1 | fragrance |

TABLE 1-continued 0.03% Retinol Wash Formulation

| Ingredient | Weight % | Function |
|---|---|---|
| Caprylic/capric triglyceride | 0.1 | Gorgonian extract antiinflammatory |
| Retinol/BHT/PMMA/TC | 0.5 | active ingredient |
| Polyethylene | 0.1 | exfoliant |
| 20% citric acid solution (aq) | 0.1 | pH adjusting agent |
| Pylam 0.1% solution (aq) | 0.3 | colorant |
| TOTAL | 100% | |

The acrylates copolymer (Carbopol Aqua SF-1; Lubrizol/Protameen) was slowly added to the water under slow agitation, followed by slow addition of the sodium laureth sulfate (Standapol ES2, Cognis/Dewolf), and the resulting mixture was heated to temperature in a range of 70-75° C. Sodium hydroxide (20% NaOH) solution then was added under slow mixing to avoid aeration and adjust pH of the mixture to a value in a range of 6.2 to 6.6. The cocamidopropyl betaine surfactant (Velvatex BK35, Cognis/Dewolf) then was added under mixing conditions, followed by mixing addition of the glycerin humectant (99.7%, kosher USP, Acme-Hardesty), PEG-8 dimethicone emollient (Zenicone DMC-1, Zenitech), the chlorphenesin preservative (Elestab CPN, Cognis/Dewolf), and methylisothiazolinone preservative (Microcare MT, Thor Specialties) to yield a first part of the formulation.

In a separate container, the cocamide MEA (Monamid CMA, Uniqema) was heated to 75° C. to melt same, following which temperature was reduced to 45° C. and the fragrance (Dove Cool Moisture Type #75457, Belle Aire) and Gorgonian extract (Gorgonian extract GC antiiflammatory, caprylic/capric triglyceride sea whip extract, Lipo) were added to the cocamide MEA and mixed until uniform, to form a second part of the formulation, which was added to the first part of the formulation, and the resulting batch of material was cooled to temperature of 30-35° C.

The retinol active ingredient (Tagravit R1, a mixture of retinol, butylhydroxytoluene (BHT), tricaprylin (TC), and polymethylmethacrylate (PMMA)), polyethylene exfoliant (Asensa SC 221, Honeywell/Tri-K), citric acid (20% aqueous solution, PCI), and Pylam colorant Blue 1 were added under mixing conditions to complete the formulation.

Example 2

A gel serum formulation was made up with the composition set out in Table 2 below.

TABLE 2

Benzoyl Peroxide Gel Serum Formulation

| Ingredient | Weight % | Function |
|---|---|---|
| Water | 76.58 | solvent/diluent |
| Disodium EDTA | 0.10 | chelating agent |
| Acrylates/C10-30 Alkyl acrylate crosspolymer | 0.20 | thickener |
| Carbomer | 0.50 | thickener |
| Acrylates/C10-30 Alkyl acrylate crosspolymer | 0.15 | thickener |
| Glycerin | 3.00 | humectant |
| Pentylene glycol | 3.00 | humectant |
| Dimethicone | 1.00 | silicone emollient |
| Caprylic/capric triglyceride | 0.50 | anti-inflammatory |
| Phenyl trimethicone | 1.00 | silicone emollient |
| Sodium hydroxide | 0.50 | pH adjuster |
| Dimethyl isosorbide | 5.00 | penetration enhancer |

TABLE 2-continued

Benzoyl Peroxide Gel Serum Formulation

| Ingredient | Weight % | Function |
| --- | --- | --- |
| Benzoyl peroxide | 6.67 | anti-acne |
| Sensiva SC-10 (trade name) | 0.80 | preservative |
| Phenoxyethanol | 1.00 | preservative |
| TOTAL | 100% | |

The disodium EDTA (NA2EDTA) was dissolved in water and then an acrylates crosspolymer (Pemulen TR1) was slowly dispersed in the water and mixed until uniform. Once uniform, the carbomer (Carbopol ultrez 10 polymer), and remaining acrylates crosspolymer (Carbopol ultrez 21 polymer) were slowly dispersed. Following dispersal, Glycerin (Glycerin 99.7% (Kosher) USP) and pentylene glycol (Hydrolite 5) were added.

Dimethicone (DC 200 Fluid 100 CST), caprylic/capric triglyceride (Gorgonian Extract GC) and phenyl trimethicone (DC 556 Fluid) were combined and slowly added to the first part of the formulation. The sodium hydroxide (Sodium hydroxide 20% solution) was then added to adjust the pH of the mixture to a value in a range of 5.0-5.75.

Dimethyl isosorbide (Arlasolve DMI-PC) and benzoyl peroxide (Luperox A75FP, Part#513474) were combined, and homogenized for 20 minutes at 3,000 RPM. The mixture was not allowed to get hot. The particle size of the benzoyl peroxide was monitored every 5-7 minutes to make certain that particles, while visible, still rubbed into the skin smoothly without feeling particulate. Following homogenization, the mixture of Dimethyl isosorbide (Arlasolve DMI-PC) and benzoyl peroxide (Luperox A75FP, Part#513474) was slowly mixed to combine with the existing formulation. The newly combined mixture was then homogenized for 10 minutes at 3,500 RPM, again the size of the benzoyl peroxide particles was monitored every 5 minutes to ensure that particles could not be felt on skin.

Sensiva SC-10 was added to the homogenized mixture by careful mixing, and then phenoxyethanol (Phenoxetol) was added to the mixture by careful mixing to complete the formulation.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A skincare composition comprising Gorgonian extract as an anti-inflammatory component thereof, said skincare composition being selected from among compositions (I) and (II):
   (I) an aqueous face wash composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %; and
   (II) a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

2. The skincare composition of claim 1, comprising an aqueous face wash composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %.

3. The skincare composition of claim 2, wherein said water and surfactant together constitute from 60 to 95 percent by weight (wt. %) of the total composition.

4. The skincare composition of claim 2, wherein the weight of surfactant to weight of water is in a ratio of from 0.40 to 1.3.

5. The skincare composition of claim 2, wherein the amount of Gorgonian extract in the composition is from 2 to 10 times the amount of retinol in the composition.

6. The skincare composition of claim 2, wherein said water and surfactant together constitute from 60 to 95% wt. % of the wash composition, based on total weight thereof.

7. The skincare composition of claim 2, wherein the surfactant comprises one or more surfactant species selected from the group consisting of sodium laureth sulfate, cocamidopropyl betaine, disodium laureth sulfosuccinate, lauryl betaine, disodium laureth sulfosuccinate, peg-10 soy sterol, sodium cocoate, sodium dodecylbenzene sulfonate, and sodium stearate.

8. The skincare composition of claim 2, further comprising thickener, humectant and emollient ingredients, consisting from 5 to 20 wt. % of the total composition weight.

9. The skincare composition of claim 2, further comprising an acrylate copolymer thickener and glycerin.

10. The skincare composition of claim 2, having a pH of between 6 and 7 and a viscosity in a range of from 3000 to 4500 centipoise, as measured by a No. 4 Brookfield spindle at a rotational speed of 20 RPM.

11. The skincare composition of claim 1, comprising a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

12. The gel composition of claim 11, wherein the total amount of benzoyl peroxide and Gorgonian extract is from 2 to 15 wt. %, based on total weight of the composition.

13. The gel composition of claim 11, wherein the weight ratio of benzoyl peroxide to Gorgonian extract is in a range of from 5 to 20.

14. The gel composition of claim 11, further comprising thickener, humectant and emollient components, wherein the thickener, humectant and emollient components have a total weight in a range of from 2 to 18 wt. %, based on total weight of the composition.

15. The gel composition of claim 11, further comprising (i) a thickener selected from the group consisting of polysaccharides, carbomers, starches, gums, waxes, sorbitols, cellulosic materials, polymers, clays, and silica, and (ii) a humectant selected from the group consisting of glycerin, propylene, alpha hydroxy acids, glyceryl triacetate, polyols, sorbitol, xylitol, maltitol, polydextrose, quillaia, lactic acid, and urea.

16. The gel composition of claim 11, having a pH of between 5 and 6.

17. The gel composition of claim 11, having viscosity in a range of from 20,000 to 40,000 centipoise, as measured under temperature-controlled conditions (Brookfield TC unit) at a rotational speed of 5 RPM.

18. A method of enhancing skin condition, comprising topically administering to skin in need thereof, a skincare composition comprising Gorgonian extract as an anti-inflammatory component thereof, said skincare composition being selected from among compositions (I) and (II):

(I) an aqueous face wash composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %; and (II) a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

19. The method of claim 18, wherein the skincare composition comprises an aqueous face wash composition comprising from 35 to 65 wt. % water, from 25 to 45 wt. % surfactant, from 0.01 to 0.2 wt. % retinol and from 0.005 to 0.5 wt. % Gorgonian extract, wherein all weight percentages are based on total weight of the aqueous face wash composition, and all weight percentages of all ingredients in the aqueous face wash composition total to 100 wt. %.

20. The method of claim 18, wherein the skincare composition comprises a gel composition comprising from 60 to 90 wt. % water, from 1 to 12 wt. % benzoyl peroxide, and from 0.05 to 1.25 wt. % Gorgonian extract, wherein all weight percentages are based on total weight of the gel composition, and all weight percentages of all ingredients in the gel composition total to 100 wt. %.

* * * * *